United States Patent [19]

McArthur

[11] Patent Number: 4,582,069
[45] Date of Patent: Apr. 15, 1986

[54] FIXATION MEANS FOR AN ENDOCARDIAL ELECTRODE

[76] Inventor: William A. McArthur, 27544 Lovage Ct., Saugus, Calif. 91350

[21] Appl. No.: 714,181

[22] Filed: Mar. 19, 1985

Related U.S. Application Data

[63] Continuation of Ser. No. 576,640, Feb. 3, 1984, abandoned.

[51] Int. Cl.⁴ ............................................... A61N 1/04
[52] U.S. Cl. .................................. 128/785; 128/419 P
[58] Field of Search .................... 128/419 P, 784, 785, 128/786

[56] References Cited

U.S. PATENT DOCUMENTS

| | | | |
|---|---|---|---|
| 3,719,190 | 3/1973 | Avery | 128/785 |
| 4,057,067 | 11/1977 | Lajos | 128/785 |
| 4,236,529 | 12/1980 | Little | 128/786 |
| 4,258,724 | 3/1981 | Balat et al. | 128/785 |
| 4,262,982 | 4/1981 | Kenny | 128/419 P |
| 4,419,819 | 12/1983 | Dickhudt et al. | 128/785 |
| 4,467,817 | 8/1984 | Harris | 128/419 P |

FOREIGN PATENT DOCUMENTS

85967  8/1983  European Pat. Off. ............ 128/785

OTHER PUBLICATIONS

1979 Medtronic Product Catalog (12 pages).
"Now There's a Long-Life Lead for Long-Life Pacers," Cordis Corporation (2 pages).
"The Cordis Finned-Tip Pervenous Ventricular Lead" Cordis Corporation, Aug. 1979 (2 pages).

*Primary Examiner*—William E. Kamm
*Attorney, Agent, or Firm*—Robert R. Meads; Bryant R. Gold

[57] ABSTRACT

An improved fixation structure for an endocardial lead (10), the lead (10) having an elongated electrical conductor (12) encased in an encasing material (14) and terminating in an exposed electrically conductive tip (16). The fixation structure includes at least one fin (20) which defines an upper edge (28), a first trailing edge portion (40), and a second trailing edge portion (42). The fin upper edge (28) defines an acute angle with respect to the longitudinal axis (22) of the lead (10). The first trailing edge portion (40) defines a ninety degree angle with respect to the longitudinal axis (22) of the electrical conductor (12) and the second trailing edge portion (42) extends backward and downward from a point (A) on the first trailing edge portion (40), until it intersects the encasing material (14) at a point (C). In one embodiment, the edge between point A and point C defines an arc. Point A begins at a point twenty percent of the distance from the encasing material (14) to the top of the first trailing edge portion (40). Thus, the fixation structure disclosed engages the heart trabeculae in substantially the same manner as other types of fixation structures. However, the second trailing portion (42) is chosen to have an edge configuration which will deflect chordae tendonae as the conductive tip is withdrawn from the heart wall for either removal or relocation. Thus, an improved endocardial fixation structure is disclosed which has the advantages of existing structures with respect to engaging heart trabeculae while at the same time facilitates tip removal in the presence of chordae tendonae in the heart.

37 Claims, 6 Drawing Figures

U.S. Patent    Apr. 15, 1986    4,582,069
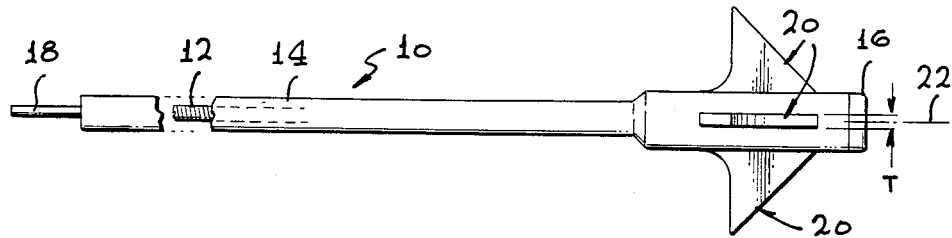
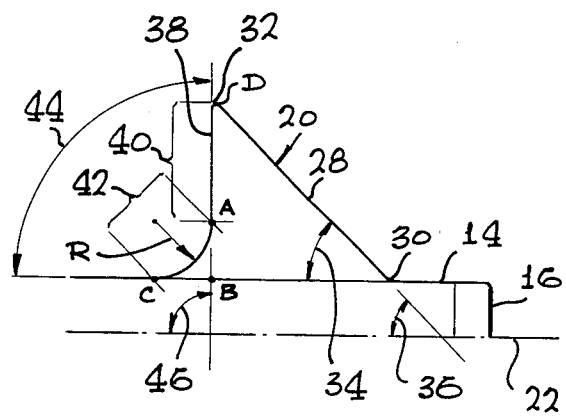
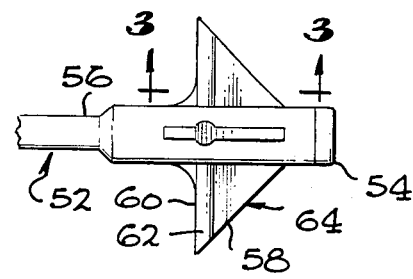
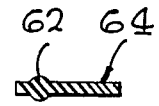
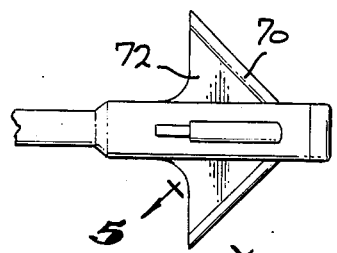
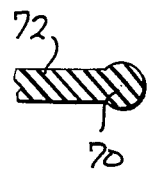

FIXATION MEANS FOR AN ENDOCARDIAL ELECTRODE

This is a continuation of co-pending application Ser. No. 576,640 filed on 02/03/84, now abandoned.

FIELD OF THE INVENTION

The invention relates to implantable endocardial leads and more particularly to endocardial leads having structures near their tips for effecting fixation in heart trabeculae.

Background Art

Endocardial leads having fixation structures near their electrode tips are old in the art. Specifically, an endocardial lead having pliant tines at the electrode tip is disclosed in U.S. Pat. No. 3,902,501 to Citron and Dickhudt. Further, leads having triangularly-shaped wedges near the electrode tip have also been utilized to enhance fixation. These leads are usually venously inserted into the heart and their electrode tips located adjacent to the heart wall. The fixation structures such as tines or triangularly-shaped wedges become enmeshed in the heart trabeculae, thus tending to fix the electrode tip in a position so that it will remain in electrical contact with and adjacent to the heart wall. However, it is sometimes required to reposition the electrode tip within the heart, or remove the lead entirely from the heart. This is usually effected by applying tension to the lead so as to disengage the fixation device from the trabeculae and to pull the electrode tip away from the heart wall. One problem that arises is that the tines of currently utilized tined leads, and the corner formed by the backward edge and lead encasing material of finned electrodes, tend to get caught in or hang up on chordae tendonae present in the heart. In other words, tines provide good fixation with heart trabeculae but snag on the chordae tendonae during repositioning. The present invention solves this problem by providing a fixation device that will entangle with the trabeculae in as efficient a manner as current fixation devices while at the same time not snagging or hanging up on chordae tendonae during electrode tip withdrawal or repositioning.

SUMMARY OF THE INVENTION

The invention solves the above problem by providing an improved endocardial lead of the type having an electrical conductor encased in an encasing material which is generally inert to body fluids. The conductor has a proximal end and a distal end terminating in a body-contact means. The improvement provided by the invention includes at least one fin attached to the encasing material, the fin having a distal end near the body-contact means and a proximal end. The fin defines an upper edge beginning at the encasing material and extending acutely away from the fin distal end and terminating at a back edge of the fin, the back edge forming a substantially ninety degree angle with respect to the conductor longitudinal axis. The invention further provides a chordae deflection means forming a part of the fin, the deflection means beginning at a point located at least ten percent of the distance from the encasing material and the top of the fin back edge. The deflection means defines an edge which extends backward and downward until it intersects the encasing material. This edge will tend to deflect chordae tendonae as the lead is removed or disengaged from heart trabeculae.

In specific embodiments of the invention, the deflection means defines an edge which is in the form of an arc extending from the fin back edge to the encasing material. This arc can be chosen to have a radius substantially the same as the radius of a trabecula in an average patient but much larger than that of the chordae tendonae. This configuration provides positive fixation or engagement with the trabeculae while at the same time allowing the chordae tendonae to slide off and not catch in the fin during lead removal. The edge of the deflecting means, however, can assume other shapes such as those of a straight line, or a stepped edge.

In further embodiments of the invention, flexure resistant portions are provided in the fin itself in order to alter the flexure characteristics of the fin as pressure is provided from various directions.

BRIEF DESCRIPTION OF THE DRAWINGS

FIG. 1 is a side view of an endocardial electrode tip according to the invention;

FIG. 1A is an enlarged view of one fin shown in FIG. 1 showing the relationship of the various parts of the fin to each other and the encasing material;

FIG. 2 shows a further embodiment of the invention;

FIG. 3 shows a cross-sectional view of one fin taken along line 3—3 of FIG. 2;

FIG. 4 shows a still further embodiment of the invention; and

FIG. 5 is a cross-sectional view taken along line 5—5 of FIG. 4.

DETAILED DESCRIPTION

Detailed illustrative embodiments of the invention disclosed herein exemplify the invention and are considered to be the best embodiments for such purposes. They are provided by way of illustration and not limitation of the invention. Various modifications thereof will occur to those skilled in the art, and such modifications are within the scope of the claims which define the present invention.

As previously explained, an endocardial lead including an electrical conductor encased in an encasing material and having improved fixation characteristics is disclosed. The endocardial lead has four fin-shaped protuberances equally spaced around the circumference of the encasing material near an electrode tip. The trailing edge of each fin defines a structure for deflecting chordae tendonae found in the heart ventricle should it be necessary to relocate the electrode tip after an initial placement. The structure for deflecting the chordae tendonae begins at a point at least ten percent of the distance between the encasing material and the top of the fin and angles backward until it intersects the encasing material. In one embodiment, the deflecting structure defines an arc having a radius equal to the distance between the beginning point of the structure and the encasing material. The fins are formed of a soft pliant material which could be the same as that utilized for the encasing material, and could be silicone rubber or polyurethane. Both of these materials exhibit sufficient rigidity to maintain the fins in an upright position when unrestrained while still allowing the fins to be deformed during placement into or removal from the heart trabeculae. The uniqueness of the deflecting structure allows chordae tendonae present within the heart ventricle to be deflected rather than snagged by the fins during electrode removal or reimplantation operations.

Referring now to FIG. 1, an endocardial lead 10 is shown having a centrally-located, spirally-wound electrical conductor 12 encased in an encasing material 14, its distal end terminating in an exposed electrically conductive tip 16. The proximal end 18 of the conductor is adapted to be removeably received by an implanted medical device such as a heart pacemaker (not shown). Four fins 20 are equally spaced around the circumference of the encasing material 14 near the electrode tip 16. These fins 20 are chosen to have a unique configuration as will be explained below which provides for firm fixation of the electrode tip 16 within the heart trabeculae while at the same time allowing less traumatic removal of the electrode tip 16 from the heart trabeculae in the event of electrode removal, replacement of reattachment operations. Although an electrode lead of a unipolar configuration is shown in FIG. 1, the invention would be equally applicable to a bipolar lead. Further, although an exposed electrically conductive tip 16 is chosen for illustrative purposes, any other body-contact device, such as a temperature sensor, ph sensor, or the like could be utilized. Although the fins 20 are shown in FIG. 1 near the electrically conductive tip 16, it should be appreciated that the fins 20 could be located in any position relative to the tip 16 so long as the interaction between the fins 20 and the heart trabeculae result in influencing the location of the tip 16 with respect to the heart wall. The longitudinal axis of the conductor 12 is shown as a dotted line 22.

Referring now to FIG. 1A, the fin 20 can be seen enlarged to illustrate its various parts and their relationship with respect to each other. The fin 20 defines an upper edge 28 which begins at a fin distal end 30 and extends upwardly and acutely away from the encasing material 14 to a point defined as a fin proximal end 32. The fin upper edge in the embodiment shown defines an angle 34 with respect to the encasing material 14 equal to forty-five degrees. Further, the fin upper edge 28 substands an angle with respect to the axis 22 also equal to forty-five degrees as shown at 36. Although forty-five degrees for the angles 34 and 36 have been chosen for illustrative purposes, the invention is in no way limited to an upper edge angle of forty-five degrees, and other angles could be utilized just so long as the angle remains acute with respect to the encasing material 14. From the fin proximal end 32, the fin defines a trailing edge 38 which for ease of explanation is defined as a first trailing edge portion 40 and a second trailing edge portion 42. The first trailing edge portion 40 can be seen as the edge defined by segment D-A; the second trailing edge portion 42 can be seen as the edge defined by segment A-C. The vertical distance between the fin proximal end 32 and the encasing material 14 can be seen to be D-B, with the second trailing edge portion 42 beginning at initiation point A. The invention requires that the distance B-A be at least ten percent of the distance B-D for reasons that will be explained in further detail below. However, in the particular embodiment shown, the distance B-A is twenty-five percent of the distance B-D, and leads have been successfully tested in animals in which the distance B-A is fifty percent of the distance B-D. Other distances such as twenty percent could also be utilized.

The second trailing edge portion 42 beginning at point A extends downward and away from the tip 16 until it intersects the encasing material 14 at point C. In the particular embodiment shown, the second trailing edge portion 42 defines an arc having a radius R as shown. Although an arc having a radius R is shown in the illustrative embodiment, it is only necessary for the trailing edge portion to extend generally downward and away from the electrode tip 16. Thus, the second trailing edge portion could define, for example, a straight line extending between A and C, or a stepped line containing a plurality of horizontal and vertical segments connecting points A and C. The requirement for C is that it be at least further from the conductive tip 16 than point B, and the requirement for point A is that it be at a point at least equal to or greater than ten percent of the distance between points B and D. In one embodiment of the invention, the radius R is equal to 0.050 inches, the thickness T of the fin is no greater than 0.040 inches, and the distance B-D shown in FIG. 1A is 0.100 inches. The radius R of 0.050 inches was chosen to be substantially equal to the radius of a trabeculae in a human heart ventricle.

In the particular embodiment shown, the angle of the first trailing edge 40 when subtended downward to intersect the encasing material at B and the conductor axis 22 is chosen to be ninety degrees as shown at 44 and 46. Although ninety degrees for the angles 44 and 46 were chosen, other angles greater than ninety degrees could be chosen.

Although in the embodiment shown, the plane of the fin 20 is parallel to the conductor axis 22, the invention is in no way limited to that configuration. For example, the plane of the fin 20 could intersect the encasing material 40 in a way to form an angle with respect to the conductor axis 22.

In operation, a lead having a fixation structure provided by the invention is veneously inserted into a patient. Pressure of the vein will cause the fins 20 to generally deform sideways, thereby tending to decrease the diameter of a circle encompassing the four fins 20. Similarly, once the tip 16 is inserted into the user's ventricle and begins to engage heart trabeculae, the fins will again deform or flex sideways as the tip 16 is pushed between trabeculae to contact the heart wall. Once the tip 16 is located within the trabeculae, the undeformed configuration of each fin 20 will tend to be restored and the fin trailing edge 38 will abut against the heart trabeculae and tend to prevent tip 16 dislodgement. However, should it be necessary for the physician to either explant the lead or reposition the conductive tip 16 to another location within the user's heart, the physician will effect this removal by applying tension along the length of the lead 10. In prior art leads during this removal, chordae tendonae within the user's heart tend to get caught in the intersection between the trailing edge of the fin and the encasing material 14. However, because of the second trailing edge portion 42 formed by the fin in accordance with the teachings of the present invention, the tendency for chordae tendonae to catch is minimized because of the characteristics of the second trailing edge as previously explained.

In the specific embodiment shown, the radius R is chosen to be close to the radius of a trabeculae within the user's heart so as to provide positive fixation or engagement with the trabeculae. However, the radius R is much larger than that of the chordae tendonae so that when the chordae tendonae come in contact with the trailing edge during tip removal, they will tend to slip upward and force the fin 20 to deform in a lateral direction for easy removal, rather than catch in a corner defined by A, B and C shown in FIG. 1A as is typical of prior art fins. Thus, the action of chordae tendonae against the fixation device provided by the present invention, rather than inhibiting removal of the electrode tip, actually facilitates removal of the electrode tip by forcing the fin 20 to move in a lateral direction as tension is applied to the lead 10.

Referring again to FIG. 1A, another way of characterizing the invention is to consider the fin portion defined by points A, B and C as a chordae tendonae deflection structure with the edge defined by A-C being a specific portion of the structure configured so as to deflect chordae from entangling with the fin defined by the proximal end 30 and points B and D. As previously explained, the portion of the chordae deflection means defined by the edge A-C could be the arc as shown in FIG. 1A, a straight edge connecting points A and C, a stepped edge connecting points A and C or any of numerous other edge configurations which generally slope downward and backward from point A until intercepting the encasing material 14 at point C. A still further way of characterizing the invention is to consider the fin and chordae deflection structure defined by the fin distal end 30 and points D, A and C as a fin-shaped fixation means having the characteristics previously described.

Referring now to FIG. 2, a further embodiment of the invention can be seen. Here, an endocardial lead 52 is shown having an exposed electrically conductive tip 54 and encasing material 56 as in the FIG. 1 embodiment. The fin upper edge 58 and fin trailing edge 60 have the characteristics as described in conjunction with FIG. 1 and FIG. 1A. However, the embodiment of FIG. 2 incorporates a supporting ridge 62 which is formed of the same pliant material as the fin 64 and is molded into the fin 64 as shown in FIG. 3 to provide increased resistance to flexure of the fin 64. As can be appreciated, the supporting ridge 62 is in the form of raised half cylinder surfaces on each side of the fin 64 which will tend to increase the resistance of the fin in moving in a lateral direction with respect to the longitudinal axis of the central conductor in the lead 52. Although in this specific embodiment, the increased flexure is provided by a thickening of the wedge as shown at 62, it should be appreciated that other means of obtaining increased flexure could be utilized such as imbedding a resilient metallic member within the fin 64, or imbedding a nonconductive material within the fin 64 that has more resistance to flexure than the material forming the fin 64. As can be seen, the specific embodiment shown in FIG. 2 shows the supporting ridge 62 being located at the proximal end of the fin 64 and oriented so that the longitudinal axis of the raised portion is perpendicular to the surface of the encasing material 56. However, it should be readily appreciated that the supporting ridge could be oriented in anyway within the fin, the specific location being dependent upon the particular flexure characteristics desired.

A still further embodiment can be seen in reference to FIGS. 4 and 5 in which a supporting ridge 70 is provided along, and defines, the upper edge of the fin 72. As can be appreciated, this is merely another way of altering the characteristics of the fin by providing an upper edge that is more likely to maintain its undeformed shape subsequent to placement within the heart trabeculae.

What is claimed is:

1. An improved endocardial lead of the type having an electrical conductor encased in an encasing material which is generally inert to body fluids, the conductor terminating in a body-contact means, the improvement comprising:

at least one fin attached to said encasing material, said fin having a distal end near said body-contact means and a proximal end, said fin defining an upper edge and a trailing edge, said upper edge beginning at said encasing material and extending acutely away from said encasing material from said fin distal end, and said trailing edge extending downward from the proximal end of said upper edge to define a first trailing edge portion and a second trailing edge portion, said first trailing edge portion defining at least a ninety degree angle with respect to the conductor axis portion extending from said fin and away from said body-contact means, said second trailing edge portion extending away from said fin proximal end until it intersects said encasing material, said second trail edge portion beginning at an initiation point no less than ten percent of the distance from the surface of said encasing material to the proximal end of said upper edge.

2. The improvement of claim 1 wherein said initiation point is located at a distance no less than twenty-five percent of the distance from the surface of said encasing material to the proximal end of said upper case.

3. The improvement of claim 2 wherein said fin is formed of a pliant material having sufficient rigidity to maintain said fin in an upright position when unrestrained, but sufficiently pliant to prevent penetration of heart tissue, said pliant material being generally inert to body fluids.

4. The improvement of claim 3 wherein said at least one fin comprises four fins equally spaced around the circumference of said encasing material.

5. The improvement of claim 3 wherein the thickness of said fin is no greater than 0.040 inches.

6. The improvement of claim 3 further comprising additional support means for altering the flexure characteristics of said fin.

7. The improvement of claim 6 wherein said additional support means comprises a thickened portion of said pliant material extending along the upper edge of said fin.

8. The improvement of claim 6 wherein said additional support means comprises a thickened portion of said pliant material extending from said encasing material to the proximal end of said upper edge.

9. The improvement of claim 8 wherein said thickened portion forms a substantially ninety degree angle with respect to the surface of said encasing material.

10. The improvement of claim 3 wherein said upper edge forms a substantially forty-five degree angle with respect to the surface of said encasing material.

11. The improvement of claim 3 wherein said upper edge forms a substantially forty-five degree angle with respect to the longitudinal axis of said electrical conductor.

12. The improvement of claim 3 wherein said body-contact means comprises an exposed, electrically conductive tip.

13. The improvement of claim 3 wherein said second trailing edge portion defines a concave arc.

14. The improvement of claim 13 wherein said concave arc has a radius of substantially 0.050 inches.

15. The improvement of claim 3 wherein said first trailing edge portion defines substantially a ninety degree angle with respect to said encasing material.

16. The improvement of claim 3 wherein said first trailing edge portion defines substantially a ninety degree angle with respect to the longitudinal axis of said electrical conductor.

17. In an endocardial lead of the type having an electrical conductor encased in an encasing material which is generally inert to body fluids, the conductor having a distal end terminating in a body-contact means and a proximal end, the improvement comprising:
  at least one fin attached to said encasing material, said fin having a distal end near said body-contact means and a proximal end, said fin defining an upper edge beginning at said encasing material and extending acutely away from said fin distal end and terminating at a back edge of said fin, said back edge forming a substantially ninety degree angle with respect to said conductor longitudinal axis; and
  chordae deflection means forming a part of said fin for deflecting endocardial chordae, said deflection means beginning at an initiation point located at least ten percent of the distance from said encasing material and the top of said fin back edge, said deflection means defining an edge which extends backward and generally downward until it intersects said encasing material.

18. The improvement of claim 17 wherein said initiation point is located at a distance at least twenty percent of the distance from said encasing material to the top of said fin back edge.

19. The improvement of claim 18 wherein said at least one fin comprises four fins.

20. The improvement of claim 18 wherein said fin is formed of a pliant material having sufficient rigidity to maintain said fin in an upright position when unrestrained, but sufficiently pliant to prevent penetration of heart tissue, said pliant material being generally inert to body fluids.

21. The improvement of claim 20 wherein the thickness of said fin is no greater than 0.040 inches.

22. The improvement of claim 20 further comprising additional support means for altering the flexure characteristics of said fin.

23. The improvement of claim 22 wherein said additional support means comprises a thickened portion of said pliant material extending along the upper edge of said fin.

24. The improvement of claim 22 wherein said additional support means comprises a thickened portion of said pliant material extending from said encasing material to the proximal end of said upper edge.

25. The improvement of claim 20 wherein said upper edge forms a substantially forty-five degree angle with respect to the surface of the encasing material.

26. The improvement of claim 20 wherein said upper edge forms a substantially forty-five degree angle with respect to the longitudinal axis of said electrical conductor.

27. The improvement of claim 20 wherein said body-contact means comprises an exposed electrically conductive tip.

28. The improvement of claim 20 wherein said deflection means edge defines a concave arc.

29. The improvement of claim 28 wherein said concave arc has a radius of approximately 0.050 inches.

30. In an endocardial lead of the type having an electrical conductor encased in an encasing material which is generally inert to body fluids, the conductor having a distal end terminating in a body-contact means, and a proximal end adapted to be received by an implanted medical device, the improvement comprising:
  fixation means attached to the electrical conductor near the body-contact means for holding the body-contact means in a desired endocardial position, said fixation means defining an edge which extends upward from said encasing material to a maximum height, then extends downward towards said encasing material to a first point at least greater than ten percent of the shortest distance between said encasing material and said point of maximum height, said edge then extending generally downward and away from said body-contact means until said edge intersects said encasing material.

31. The improvement of claim 30 wherein said first point is at a distance at least greater than twenty-five percent of the shortest distance between said encasing material and said point of maximum height.

32. The improvement of claim 31 wherein said at least one fin-shaped fixation means is formed of a pliant material having sufficient rigidity to maintain said fin in an upright position when unrestrained, but sufficiently pliant to prevent penetration of heart tissue, said pliant material being generally inert to body fluids.

33. The improvement of claim 32 wherein the plane of said at least one fin-shaped fixation means is substantially parallel to the longitudinal axis of said electrical conductor.

34. The improvement of claim 32 wherein said at least one fin-shaped fixation means comprises four fin-shaped fixation means.

35. The improvement of claim 32 wherein the edge which extends upward from said encasing material to a maximum height forms approximately a forty-five degree angle with respect to the conductor axis.

36. The improvement of claim 32 wherein the edge which extends downward from said maximum height to said first point forms substantially a ninety degree angle with respect to said encasing material.

37. The improvement of claim 32 wherein the edge which extends downward from said maximum height to said first point forms substantially a ninety degree angle with respect to the longitudinal axis of said electrical conductor.

* * * * *